United States Patent
Caboche

(12) 
(10) Patent No.: US 6,350,864 B1
(45) Date of Patent: Feb. 26, 2002

(54) PROCESS FOR THE PREPARATION OF A MIXTURE OF GLUCOSYLMANNITOL AND GLUCOSYLSORBITOL BY THE HYDROGENATION OF GLUCOSYLGLUCOSONE

(75) Inventor: Jean-Jacques Caboche, Drouvin le Marais (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/571,655

(22) Filed: May 15, 2000

(30) Foreign Application Priority Data

May 17, 1999 (FR) ............................................... 99 06226

(51) Int. Cl.[7] .......................... C07G 3/00; C07G 11/00; C07G 17/00; C07H 15/00; C07H 1/00
(52) U.S. Cl. ..................... 536/18.5; 536/1.11; 536/4.1; 536/124
(58) Field of Search ............................... 536/18.5, 1.11, 536/4.1, 124

(56) References Cited

U.S. PATENT DOCUMENTS

| | | | |
|---|---|---|---|
| 4,521,252 A | 6/1985 | Miyake et al. ............. | 127/46.3 |
| 4,684,720 A | 8/1987 | Darsow et al. ............. | 536/124 |
| 5,644,044 A | 7/1997 | Darsow ...................... | 536/18.5 |
| 5,856,469 A | 1/1999 | Duflot et al. ............... | 536/124 |
| 6,020,720 A | 2/2000 | Darsow ...................... | 536/18.5 |

FOREIGN PATENT DOCUMENTS

| | | |
|---|---|---|
| WO | WO84/00778 | 3/1984 |
| WO | WO88/05767 | 8/1988 |

OTHER PUBLICATIONS

Huwig, Med. Fac. Landbouww. Univ. Gent., pp 1193–1197, 1997.
Volc, Arch. Microb., vol. 167, pp 119–125, 1997.
Strater, P.J., Chap 11 Alternative Sweetners, 1986.
Abstract in English of WO97/19093.

Primary Examiner—Jezia Riley
(74) Attorney, Agent, or Firm—Henderson & Sturm LLP

(57) ABSTRACT

The invention relates to a process for the preparation of a mixture of glucosylmannitol and glucosylsorbitol, characterized in that glucosylglucosone is hydrogenated, in the presence of a catalyst, by subjecting a glucosylglucosone solution with a solids content equal to at least 10% by weight, preferably of between 20 and 50% by weight, to a pressure equal to at least 30 bar, preferably of between 30 and 200 bar, and to a temperature equal to at least 50° C., preferably of between 50 and 150° C.

19 Claims, No Drawings

PROCESS FOR THE PREPARATION OF A MIXTURE OF GLUCOSYLMANNITOL AND GLUCOSYLSORBITOL BY THE HYDROGENATION OF GLUCOSYLGLUCOSONE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to a process for the preparation of a mixture of glucosylmannitol and glucosylsorbitol by the hydrogenation of glucosylglucosone.

The invention relates in particular to a process for the preparation of a mixture of glucosylmannitol and glucosylsorbitol by the hydrogenation of glucosylglucosone, in the presence of a catalyst, using specific hydrogenation pressure and temperature conditions for a high glucosylglucosone solids content.

The present invention relates more precisely to a process for the preparation of a mixture of glucosylmannitol and glucosylsorbitol by the continuous hydrogenation of glucosylglucosone in a fixed catalyst bed, and more particularly to the implementation of this continuous process in a succession of fixed catalyst beds arranged in series and in at least two reaction zones.

Finally, the present invention relates to a mixture of glucosylmannitol and glucosylsorbitol, especially a mixture of α-1,4-linked or α-1,6-linked isomers of glucosylmannitol and glucosylsorbitol, containing at least an equimolar proportion of glucosylmannitol and glucosylsorbitol.

2. Description of the Prior Art

These mixtures of α-1,4-linked or α-1,6-linked isomers are conventionally prepared either by mixing each of the two components in the desired proportions or by isomerizing or epimerizing specific disaccharides.

Thus glucosyl-α-1,4-mannitol and glucosyl-α-1,4-sorbitol (or maltitol) can be produced separately and then combined to give the expected mixture.

However, although maltitol is easy to prepare by hydrogenating a maltose syrup obtained from a starch hydrolyzate by any means conventionally known to those skilled in the art, glucosyl-α-1,4-mannitol is prepared by a step involving isolation of the rare sugar glycosyl-α-1,4-mannose from complex media (extracts of algae or yeasts, for example) by expensive and complex processes with very low yields, followed by a hydrogenation step.

As regards the α-1,6-linked isomers, the corresponding mixture of the two components glucosylmannitol and glucosylsorbitol in equimolar proportions is known to those skilled in the art by the name palatinitol.

Palatinitol is a low-calorie bulk sweetener with a low cariogenicity; it is obtained e.g. by the catalytic hydrogenation of isomaltulose, or glucosyl-α-1,6-fructose, at neutral pH.

Isomaltulose itself is obtained by the enzymatic isomerization of sucrose, or glucosyl-α-1,2-fructose, with the aid of a sucrose glycosyltransferase.

Among other documents relating to the preparation and properties of palatinitol, reference may be made to the book "Alternative Sweeteners" published in 1986 by LYN O'BRIEN NABORS, chap. 11, pp. 217–244.

However, this isomerization process only affords a roughly equimolar mixture of glucosyl-α-1,6-mannitol and glucosyl-α-1,6-sorbitol (or isomaltitol) without the possibility of varying the relative composition of the two constituents in the mixture.

In patent applications WO 97/19093 and WO 97/19094, of which the Applicant is the proprietor, it was shown that palatinitol could also be prepared from isomaltose, or glucosyl-α-1,6-glucose.

Isomaltose in turn is prepared from glucose or a maize syrup as described for example in patent application FR 2.515.186.

However, although these alternative processes make it possible to obtain palatinitol without being obliged to use sucrose as the starting material, it is nevertheless the case that this mixture of glucosyl-α-1,6-mannitol and glucosyl-α-1,6-sorbitol can still only be obtained in equimolar proportions.

At best the final mixture can contain a high proportion of glucosyl-α-1,6-sorbitol if the chromatography techniques normally employed in the processes of patent applications WO 97/19093 and WO 97/19094 for separating the components of said mixture to give an equimolar mixture are not used.

Also, the mixture can advantageously be enriched in isomaltitol simply by adding said compound obtained elsewhere by the catalytic hydrogenation of isomaltose.

It is apparent from all the above that there is an unsatisfied need for a simple process which makes it possible in the vast majority of cases to obtain a mixture of glucosylmannitol and glucosylsorbitol, irrespective of the type of linkage isomer in question, in at least equimolar proportions and, more particularly, enriched in its glucosylmannitol component.

DETAILED DESCRIPTION OF THE INVENTION

Anxious to develop a process which makes it possible to meet practical constraints better than the processes already in existence, the Applicant found that this objective could be achieved by a process for the catalytic hydrogenation of glucosylglucosone carried out under specific temperature and pressure conditions.

"Glucosone", also known as 2-ketoglucose or D-arabino-2-hexulosone, is understood as meaning the product resulting from the chemical treatment of glucose with hydrogen peroxide or with copper acetate or, advantageously, the product resulting from the enzymatic conversion of glucose with the aid of a pyranose-2-oxidase.

It is further known in the state of the art that pyranose-2-oxidase also has a broad spectrum of enzymatic modification.

Thus, in Med. Fac. Landbouww. Univ. Gent., 62/4a, 1997, pp. 1193–1197, HUWIG et al. show that pyranose-2-oxidase isolated from *Peniophora gigantea* is capable of reacting with isomaltose to give the oxidation product of its glucose in the terminal reducing position, i.e. glucosyl-α-1,6-glucosone.

Likewise, in Arch. Microbiol., 1997, 167, pp. 119–125, VOLC et al. show that pyranose-2-oxidase isolated from *Agaricus bisporus* reacts with maltose to give glucosyl-α-1,4-glucosone.

However, nowhere do these documents describe or suggest that it is possible advantageously to use these two α-1,4-linked and α-1,6-linked isomers of glucosylglucosone to give, by means of a specific hydrogenation process, a mixture of glucosylmannitol and glucosylsorbitol in at least equimolar proportions, and more particularly at mixture containing a high proportion of glucosylmannitol preferably equal to at least 1.5.

To its credit the Applicant therefore found a process for the preparation of a mixture of glucosylmannitol and glucosylsorbitol which is characterized in that glucosylglucosone is hydrogenated, in the presence of a catalyst, by subjecting a glucosylglucosone solution with a solids content equal to at least 10% by weight, preferably of between 20 and 50% by weight, to a pressure equal to at least 30 bar, preferably of between 30 and 200 bar, and to a temperature equal to at least 50° C., preferably of between 50 and 150° C.

In this way the Applicant found that the process according to the invention makes it possible to hydrogenate the α-1,4-linked and α-1,6-linked isomers of glucosylglucosone equally well.

The process according to the invention uses a glucosylglucosone solution with a solids content equal to at least 10% by weight, preferably of between 20 and 50% by weight.

Glucosylglucosone of very high purity, advantageously produced from maltose or isomaltose enzymatically by any means known per se to those skilled in the art, is chosen for the preparation of the solution to be hydrogenated. The choice of the α-1,4-linked or α-1,6-linked isomer of glucosylglucosone as the starting material to be hydrogenated is then based on the nature of the mixture of glucosylmannitol and glucosylsorbitol which it desired to obtain.

"High purity" is understood as meaning a glucosylglucosone content in the order of 100%.

The catalyst is selected from the group consisting of palladium, nickel, ruthenium, platinum, rhodium, cobalt, copper, zinc, chromium, manganese and tungsten and is preferably nickel.

In one preferred embodiment of the process according to the invention, in which the catalyst is suspended in the glucosylglucosone solution to be hydrogenated, it is advantageous to choose nickel in its form known as Raney Ni.

In another preferred embodiment of the process according to the invention, the catalyst can be impregnated or co-exchanged on an inert support preferably selected from the group consisting of active charcoal, peat, zeolites, aluminosilicates and titanium dioxide. It preferably consists of active charcoal.

The weight ratio catalyst/inert support is advantageously set at a value of between 1 and 5%, preferably in the order of 2%.

It is also possible to use a catalyst containing a promoter. This promoter can be selected from the group consisting of titanium, molybdenum and platinum.

In one embodiment of the process according to the invention, a suspension of glucosylglucosone with a solids content of between 10 and 50% is prepared and the catalyst is introduced in its Raney Ni form.

In this case it is chosen to use a hydrogenation pressure equal to at least 30 bar, preferably of between 30 and 200 bar and particularly preferably in the order of 100 bar, and a temperature equal to at least 50° C., preferably of between 50 and 150° C. and particularly preferably a temperature in the order of 125° C.

The pressure conditions are generally chosen to substantially avoid hydrolysis, even partial hydrolysis, of the glucosylglucosone to glucose and glucosone, which is likely to result in the appearance of fructose, sorbitol or mannitol in the final mixture of glucosylmannitol and glucosylsorbitol.

In another embodiment of the process according to the invention, it is chosen to carry out the hydrogenation in a continuous mode on a fixed catalyst bed.

In this case the catalyst is arranged in a fixed bed in the form of a compact stack of particles, the whole being placed on supporting grids in a hydrogenation reactor. It is advantageous to choose a trickle-flow reactor.

In terms of the invention, "trickle-flow reactor" is understood as meaning a hydrogenation reactor in which a liquid phase, containing the product to be hydrogenated, and a gas phase circulate in co-current or counter-current, preferably in co-current from top to bottom, through a fixed bed of catalyst particles in which the hydrogenation reaction takes place.

The flow rates of these two phases are regulated so as to allow the liquid to trickle over said catalyst particles and ensure the best contact between the two liquid and gaseous phases on the one hand and the solid catalyst phase on the other.

In one embodiment of the process according to the invention, it is chosen to prepare a fixed bed consisting of 200 l of commercial catalyst, the chosen value of the feed rate of the glucosylglucosone solution with a solids content of between 10 and 50% by weight is between 150 and 250 kg/h and the chosen amount of hydrogen introduced into said trickle-flow reactor is in the order of two to fifteen times the stoichiometry of the reaction.

In this case the hydrogenation pressure and temperature used are advantageously chosen to have respective values in the order of 30 to 150 bar, for example 150 bar, and in the order of 50 to 150° C., for example 90° C.

The mixture of glucosylmannitol and glucosylsorbitol is then obtained in equimolar proportions and with a conversion yield equal to at least 90%.

In one preferred embodiment of the process according to the invention, it is chosen to carry out a continuous process for the hydrogenation of glucosylglucosone in a succession of fixed catalyst beds arranged in series and in at least two reaction zones.

In this case the hydrogenation is advantageously carried out in a first reaction zone, consisting of at least one fixed catalyst bed, to give a high conversion of the glucosylglucosone to a mixture of glucosylmannose, glucosylfructose and glucosylglucose containing a high proportion of glucosylmannose, and then in a second reaction zone, consisting of at least one fixed catalyst bed, in which hydrogenation is carried out to give a mixture of glucosylmannitol and glucosylsorbitol with a high degree of conversion and a high proportion of glucosylmannitol.

The Applicant thus found that it is possible to carry out the hydrogenation in a continuous mode and in at least two reaction zones, so as to separate the step involving the production of the mixture of glucosylmannose, glucosylfructose and glucosylglucose from the step involving the production of the mixture of glucosylmannitol and glucosylsorbitol, to give the mixture of glucosylmannitol and glucosylsorbitol with a high glucosylmannitol content never previously achieved, and with a high productivity and a high degree of conversion.

It is possible to use different kinds of catalyst in each of the reaction zones, but it is preferred to use the same kind of catalyst in both these zones.

In the first reaction zone, the pressure conditions are regulated so as to give a high conversion, equal to at least 80%, of glucosylglucosone to a mixture of glucosylmannose, glucosylfructose and glucosylglucose containing a high proportion of glucosylmannose.

In terms of the invention, "high proportion of glucosylmannose" is understood as meaning a glucosylmannose content equal to at least 40% by weight, preferably equal to at least 70% by weight of the mixture.

The hydrogenation pressure in the first reaction zone is set at a value equal to at least 50 bar and of between 50 and 100 bar, preferably in the order of 80 bar.

In the second reaction zone, the pressure conditions are regulated so as to give the mixture of glucosylmannitol and glucosylsorbitol, containing a high proportion of glucosylmannitol, with a degree of conversion equal to at least 95%.

In terms of the invention, "high proportion of glucosylmannitol" is understood as meaning a weight ratio glucosylmannitol/glucosylsorbitol equal to at least 1.5.

The hydrogenation pressure in the second reaction zone is set at a value equal to at least 100 bar and of between 100 and 200 bar, preferably in the order of 150 bar.

The hydrogenation temperature is preferably kept constant in the two reaction zones at a value of between 50 and 100° C. and in the order of 90° C., as exemplified below.

The fixed catalyst beds are advantageously arranged in trickle-flow reactors. It is chosen to use 200 l of commercial catalyst particles, the chosen value of the feed rate of the glucosylglucosone solution with a solids content of between 10 and 50% by weight is between 200 and 300 kg/h and the chosen amount of hydrogen is between two and fifteen times the stoichiometry of the reaction.

Other characteristics and advantages of the invention will become apparent from the non-limiting Examples described below.

EXAMPLE 1

The hydrogenation reaction is carried out in a single trickle-flow reactor containing a single fixed bed of nickel-on-charcoal catalyst through which hydrogen and a glucosyl-$\alpha$-1,6-glucosone solution are circulated in co-current from the top to the bottom of said reactor.

The fixed bed of nickel catalyst consists of a compact stack of cylindrical grains of catalyst.

Each grain of catalyst is composed of NORIT RX08 active charcoal, in the form of a cylinder 0.8 mm in diameter and 1 to 5 mm in length, containing 2% by weight of nickel.

The reactor contains in the order of 200 l of catalyst arranged in a fixed bed 30 cm in diameter and in the order of 3 m in height.

A glucosylglucosone solution with a solids content of 30%, and hydrogen, are fed into the reactor simultaneously at rates of 200 kg/h and 12 kg/h respectively.

The operating pressure in the reactor is 150 bar and the temperature is 110° C.

The degree of conversion obtained at the reactor outlet is 92.5% and the ratio glucosyl-$\alpha$-1,6-mannitol/glucosyl-$\alpha$-1,6-sorbitol in the mixture is equimolar.

EXAMPLE 2

The hydrogenation reaction is carried out in two trickle-flow reactors connected in series with an intermediate heat exchanger.

The two reactors each contain a single fixed bed of nickel-on-charcoal catalyst through which hydrogen and a glucosyl-$\alpha$-1,4-glucosone solution are circulated in co-current from the top to the bottom of said reactors.

Each fixed bed of nickel catalyst consists of a compact stack of cylindrical grains of catalyst.

Each grain of catalyst is composed of NORIT RX08 active charcoal, in the form of a cylinder 0.8 mm in diameter and 1 to 5 mm in length, containing 2% by weight of nickel.

Each reactor contains in the order of 200 l of catalyst arranged in a fixed bed 30 cm in diameter and in the order of 3 m in height.

A glucosylglucosone solution with a solids content of 30%, and hydrogen, are fed simultaneously into the first hydrogenation zone at rates of 250 kg/h and 12 kg/h respectively.

The operating pressure in the first reactor is 80 bar and the temperature is 90° C.

The temperature at the inlet of the second reactor is kept at 90° C. and the pressure is set at 150 bar.

The degree of conversion at the outlet of the first reactor is 75% and the mixture of glucosyl-$\alpha$-1,4-mannose, glucosyl-$\alpha$-1,4-fructose and glucosyl-$\alpha$-1,4-glucose has the following composition: 65% by weight of glucosyl-$\alpha$-1,4-mannose, 15% of glucosyl-$\alpha$-1,4-fructose and 20% of glucosyl-$\alpha$-1,4-glucose.

The conversion at the outlet of the second reactor is 98% and the mixture of glucosyl-$\alpha$-1,4-mannitol and glucosyl-$\alpha$-1,4-sorbitol has a ratio glucosyl-$\alpha$-1,4-mannitol/glucosyl-$\alpha$-1,4-sorbitol of 2.5.

What is claimed is:

1. A process for the preparation of a mixture of glucosylmannitol and glucosylsorbitol, wherein glucosylglucosone is hydrogenated, in the presence of a catalyst, by subjecting a glucosylglucosone solution with a solids content equal to at least 10% by weight, to a pressure equal to at least 30 bar, and to a temperature equal to at least 50° C.

2. Process according to claim 1, wherein the catalyst is selected from the group consisting of palladium, nickel, ruthenium, platinum, rhodium, cobalt, copper, zinc, chromium, manganese and tungsten and is preferably nickel.

3. Process according to claim 1, wherein the hydrogenation of the glucosylglucosone is carried out in a continuous mode on one or more fixed catalyst beds.

4. Process according to claim 3, wherein the continuous hydrogenation is carried out on at least one fixed catalyst bed in which the pressure is between 30 and 150 bar and the temperature is between 50 and 150° C.

5. The process according to claim 3, wherein the continuous hydrogenation of glucosylglucosone is carried out in a succession of fixed catalyst beds arranged in series, which comprises:

a first hydrogenation zone, consisting of at least one fixed catalyst bed, in which the pressure is equal to at least 50 bar; and a second hydrogenation zone, consisting of at least one fixed catalyst bed, in which the pressure is equal to at least 100 bar.

6. Process according to claim 5, wherein the hydrogenation temperature in both reaction zones is between 50 and 100° C.

7. The process according to claim 1, wherein the glucosylglucosone is selected from the group of glucosylglucosone linkage isomers consisting of glucosyl-$\alpha$-1,4-glucosone and glucosyl-$\alpha$-1,6-glucosone.

8. Mixture of glucosyl-α-1,4-mannitol and glucosyl-α1, 4-sorbitol in a ratio glucosyl-α1,4-mannitol/glucosyl-α1,4-sorbitol equal to at least 1, obtainable by carrying out a process according to claim 1.

9. The process for the preparation of a mixture of glucosylmannitol and glucosylsorbitol according to claim 1, wherein said solids content is between 20% and 50% by weight.

10. The process for the preparation of a mixture of glucosylmannitol and glucosylsorbitol according to claim 1, wherein said pressure is between 30 and 200 bar.

11. The process for the preparation of a mixture of glucosylmannitol and glucosylsorbitol according to claim 1, wherein said temperature is between 50° C. to 150° C.

12. The process for the preparation of a mixture of glucosylmannitol and glucosylsorbitol according to claim 1, wherein wherein said solids content is between 20% and 50% by weight, wherein said pressure is between 30 and 200 bar, and wherein said temperature is between 50° C. to 150° C.

13. The process according to claim 5, wherein for said first hydrogenation zone, the pressure is between 50 and 100 bar.

14. The process according to claim 5, wherein for said second hydrogenation zone, the pressure is between 100 and 200 bar.

15. The process according to claim 5, wherein for said first hydrogenation zone, the pressure is between 50 and 100 bar, and wherein for said second hydrogenation zone, the pressure is between 100 and 200 bar.

16. The process according to claim 13, wherein the hydrogenation temperature in both reaction zones is between 50 and 100° C.

17. The process according to claim 14, wherein the hydrogenation temperature in both reaction zones is between 50 and 100° C.

18. The process according to claim 15, wherein the hydrogenation temperature in both reaction zones is between 50 and 100° C.

19. Mixture of glucosyl-α1,4-mannitol and glucosyl-α1, 4-sorbitol in a ratio glucosyl-α1,4-mannitol/glucosyl-α1,4-sorbitol equal to at least 1.5, obtainable by carrying out a process according to claim 1.

* * * * *